(12) United States Patent
Hsieh

(10) Patent No.: US 7,527,812 B2
(45) Date of Patent: May 5, 2009

(54) HERBAL COMPOSITION FOR TREATING CANCER

(75) Inventor: Chen Fung Hsieh, Taipei (TW)

(73) Assignee: Sheng Foong Pharmaceutical Co., Ltd., Taipei (TW)

( * ) Notice: Subject to any disclaimer, the term of this patent is extended or adjusted under 35 U.S.C. 154(b) by 0 days.

(21) Appl. No.: 11/535,483

(22) Filed: Sep. 26, 2006

(65) Prior Publication Data

US 2007/0082072 A1    Apr. 12, 2007

(30) Foreign Application Priority Data

Oct. 6, 2005   (DE)   ............... 20 2005 015 707 U

(51) Int. Cl.

| | |
|---|---|
| *A01N 65/00* | (2006.01) |
| *A61K 36/258* | (2006.01) |
| *A61K 36/481* | (2006.01) |
| *A61K 36/236* | (2006.01) |
| *A61K 36/355* | (2006.01) |
| *A61K 36/00* | (2006.01) |
| *A61K 36/254* | (2006.01) |
| *A61K 36/48* | (2006.01) |

(52) U.S. Cl. .................. 424/725; 424/773; 424/728; 424/757

(58) Field of Classification Search ............... None
See application file for complete search history.

(56) References Cited

U.S. PATENT DOCUMENTS

| | | | | |
|---|---|---|---|---|
| 4,613,591 | A | * | 9/1986 | Aburada et al. ............ 514/34 |
| 5,837,257 | A | * | 11/1998 | Tsai et al. ................. 424/741 |
| 2002/0182274 | A1* | | 12/2002 | Lu ............................ 424/757 |
| 2003/0228379 | A1* | | 12/2003 | Shi et al. .................. 424/725 |
| 2004/0076641 | A1* | | 4/2004 | Kershenstine, Jr. ...... 424/195.15 |

FOREIGN PATENT DOCUMENTS

| | | | | |
|---|---|---|---|---|
| CN | 1220891 | A | * | 6/1999 |
| CN | 1421224 | A | * | 6/2003 |
| CN | 1470276 | A | * | 1/2004 |
| JP | 360025933 | | * | 2/1985 |

OTHER PUBLICATIONS

Xiang., Chinese Gall Nut Aphids on Rhus-Potaninii. Entomotaxonomia, (1980) vol. 2, No. 4, pp. 303-313.*
Freshney, Culture of Animal Cells, A Manual of Basic Technique, Alan R. Liss, Inc., 1983, New York, p. 4.*
Dermer, Bio/Technology, 1994, 12:320.*
Gura (Science, v278, 1997, pp. 1041-1042).*
MSNBC News Services, "Mixed results on new cancer drug", Nov. 9, 2000.*
Shao BM et al., A study on the immune receptors for polysaccharides from the roots of *Astragalus membranaceus*, a Chinese medicinal herb., Aug. 6, 2004;320(4):1103-11, Biochem Biophys Res Commun.
Takara K et al., Effects of 19 Herbal Extracts on the Sensitivity to Paclitaxel or 5-Fluorouracil in hela Cells., Jan. 2005;28(1):138-42, Biol Pharm Bull.
Niwa K. et al., Preventive Effects of Glycyrrhizae radix Extract on Estrogen-related Endometrial Carcinogenesis in Mice, Jul. 1999; 90(7):726-32, Jpn J Cancer Res.
Lian Z, et al., Herbal complex suppresses telomerase activity in chemo-endocrine resitant cancer cell lines, 2001; 22 (5): 347-9, Eur J Gynaecol Oncol.
Lian Z, et al., Association of cellular apoptosis with anti-tumor effects of the Chinese herbal complex in endocrine-resistant cancer cell line, 2003;27(2):147-54, Cancer Detect Prev.
Kim OS, et al., Establishment of In Vitro Test System for the Evaluation of the Estrogenic Activities of Natural Products, Sep. 2004;27(9):906-11, Arch Pharm Res.
Loo WT, et al., The inhibitory effect of a herbal formula comprising ginseng and *Carthamus tinctorius* on breast cancer, Nov. 26, 2004;76(2):191-200, Life Sci.
095136827; Taiwan Office Action; May 2, 2008; Taiwan.

* cited by examiner

*Primary Examiner*—Michael V Meller
*Assistant Examiner*—Qiuwen Mi
(74) *Attorney, Agent, or Firm*—WPAT, PC; Anthony King

(57) ABSTRACT

An herbal composition that provides anti-cancer effects, especially for breast cancer.

4 Claims, 4 Drawing Sheets

A498 - SF-01 5mg

A498 - control

HCT-116 - SF-01 5mg

HCT-116 - control

MCF-7 - SF-01 5mg

MCF-7 - control

NPC-TW01 - SF-01 5mg

NPC-TW01 - control

RPTEC - SF-01 5mg

RPTEC - control

Hep 3B SF-01 5mg

Hep 3B control

LNCaP SF-01 5mg

LNCaP control

MKN45 SF-01 5mg

MKN45 control

NCI-H226 SF-01 5mg

NCI-H226 control

HERBAL COMPOSITION FOR TREATING CANCER

FIELD OF THE INVENTION

The present invention relates to a herbal composition for treating cancer, especially for breast cancer.

BACKGROUND OF THE INVENTION

The popularity of traditional herbal medicine being used as complementary medicines or alternative medicines is rapidly increasing in recent years. The current understanding on the molecular mechanisms of immunopotentiating polysaccharides from medicinal herbs have provided important clues on the anti-cancer effects of Chinese herbal medicines [Shao BM, et al., Biochem Biophys Res Commun. 2004 Aug. 6;320 (4):1103-11]. Also, it was found that the combination of anticancer drugs with some herbal extracts contributes to the enhancement of clinical outcomes in cancer chemotherapy [Takara K, et al., Biol Pharm Bull. 2005 Jan.; 28(1):138-42]. Chinese herbal medicines have emerged as an effective tool for treating cancer.

In previous publications, several herbal compounds or complexes have been indicated to be candidate drugs for treating breast cancer. For example, the *Glycyrrhizae radix* extract was suggested to exhibit inhibitory effects on E2-related endometrial carcinogenesis in mice [Niwa K. et al., Jpn J Cancer Res. 1999 Jul.; 90(7):726-32]. A herbal complex consisting of Hoelen, *Angelicae radix, Scutellariae radix* and *Glycyrrhizae radix* suppresses the tumor growth of chemoendocrine resistant cancers [Lian Z, et al., Eur J Gynaecol Oncol. 2001; 22(5): 347-9]. Still another herbal complex consisting of Hoelen, *Angelicae radix, Scutellariae radix* and *Glycyrrhizae radix* is shown to be a potential candidate for treating endocrine-resistant gynecologic carcinomas [Lian Z, et al., Cancer Detect Prev. 2003;27(2):147-54]. In addition, it is suggested that *Puerariae radix* and *Ginseng radix* Rubra extracts have effective estrogenic actions and could be developed as estrogenic supplements [Kim OS, et al., Arch Pharm Res. 2004 Sep.;27(9):906-11]. Furthermore, the complex named Zhu-xiang containing ginseng and *Carthamus tinctorius* also exhibits the ability to inhibit proliferation in MDA-MB-231 breast cancer cell [Loo WT, et al., Life Sci. 2004 Nov. 26;76(2):191-200]. These herbal medicines have shed some lights on the therapy of breast cancer.

All of the above-mentioned references are herein incorporated by reference in their entireties.

SUMMARY OF THE INVENTION

The present invention relates to a herbal composition, comprising wubeizi, *Lonicera japonica, Astragalus membranaceus, Rehmanniae Radix, Glycyrrhizae Radix* and *Panax schinseng*. The weight ratios of any two components range from 1:10 to 10:1.

DETAILED DESCRIPTION OF THE INVENTION

Figure 1:
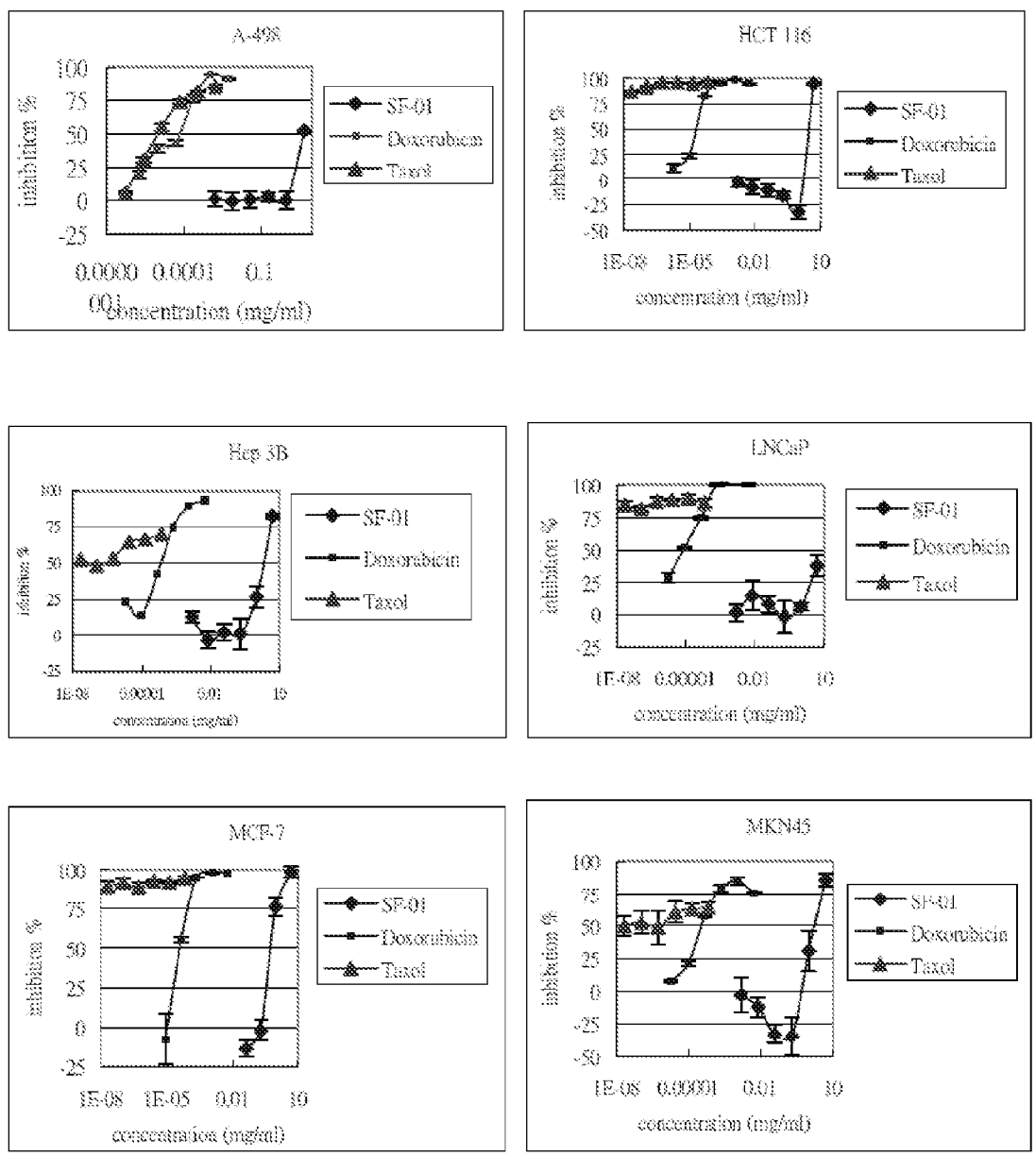
FIG. 1 shows the inhibitory effects of the composition of the present invention, Taxol and Doxorubicin on cell growth of human cancer cell A498, HCT 116, Hep 3B, LNCaP clone FGC, MCF-7, MKN45, NCI-H226, NPC-TW01 and the human normal renal cell RPTEC.
Figure 1:
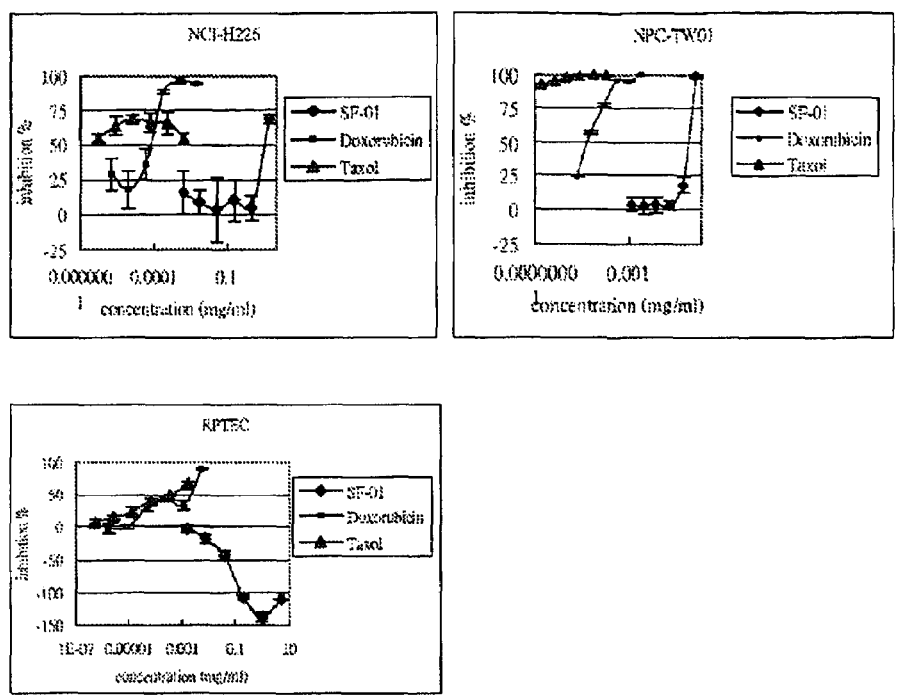

The present invention relates to a herbal composition that provides anti-cancer effects, especially for breast cancer.

Herbal Composition

The present invention relates to a composition of herbal medicines comprising Wubeizi, *Lonicerajaponica, Astragalus membranaceus, Rehmanniae Radix, Glycyrrhizae Radix* and *Panax schinseng*.

Wubeizi is the gall produced by the parasitic aphids *Melaphis chinensis* (Bell) Baker on the leaves or stems of a plant selected from the group consisting of *Rhus chinensis* Mill, *Rhus potaninii* Maxim and *Rhus punjabensis* Stew. var. sinica (Diels) Rehd. et Wils.

*Lonicera japonica* is prepared from the flower buds of a plant selected from the group consisting of *Lonicerajaponica* and *Lonicera confuse*.

*Astragalus membranaceus* is prepared from the roots of a plant selected from the group consisting of *Astragalus membranaceus* (Fisch.) Bge. and *Astragalus membranaceus* Bge. var. mongholicus (Bge.) Hsiao.

*Rehmanniae Radix* is prepared from the roots of *Rehmannia glutinosa* Libosch.

*Glycyrrhizae Radix* is prepared from the whole plant of a plant selected from the group consisting of *Glycyrrhiza uralensis* Fisch., *Glycyrrhiza glabra* L., *Glycyrrhiza kansuensis* Chang et Peng and *Glycyrrhiza inflata* Batal.

*Panax schinseng* is prepared from the roots of a plant selected from the group consisting of *Panax schinseng* and *Panax pseudoginseng*.

The weight ratios of any two components in the composition of the present invention range from 1:10 to 10:1. In a preferred embodiment, the weight ratios of any two components range from 1:7 to 7:1. In a more preferred embodiment, the weight ratios of any two components range from 1:5 to 5:1. In a furthermore preferred embodiment, the weight ratios of any two components range from 1:3 to 3:1. In the most preferred embodiment, the weight ratio of wubeizi, *Lonicerajaponica, Astragalus membranaceus, Rehmanniae Radix, Glycyrrhizae Radix* and *Panax schinseng* is 1:1:1:1:1:1.

Anti-cancer Effects

The present composition can induce the apoptosis of the cancer cell in accordance with this invention. The cancer cells include abnormal cancer cells associated with lymphoma, leukemia, plasma cell dyscrasias, multiple myeloma, amylodosis, also as known as hepatocellular cancer, colorectal cancer, renal cancer, breast cancer, prostate cancer, stomach cancer, lung cancer, nasal-pharyngeal cancer, ovarian cancer, bone cancer, gastric cancer, pancreatic cancer, and melanoma. In a preferred embodiment, the present composition can induce apoptosis of the tumor cells of hepatocellular cancer, colorectal cancer, renal cancer, breast cancer, prostate cancer, stomach cancer, lung cancer and nasal-pharyngeal cancer. In the most preferred embodiment, the present composition induces apoptosis of breast cancer cells.

EXAMPLES

The examples below are non-limiting and are merely representative of various aspects and features of the present invention.

Example 1

Preparation of Single-herb Herbal Medicines

A whole herb of medicinal plant was obtained, washed with cold water and dried. The plant materials were then extracted with boiling water. The weight ratio of plant material to water was approximately 1:5 to 1:10. The amount of water used should at least cover the plant material in the extraction vessel. To allow effective extraction of the desired components, samples were boiled for 0.5 to one hour, but not more than 3 hours. Then, the aqueous solution was separated from the plant residues by filtration. After that, the aqueous solution was spray-dried, freeze-dried or absorbed by powdered material of starch. The single-herb herbal medicine was prepared in powdered form.

Example 2

Preparation of the Composition of the Invention

The herb mixture was prepared by mixing six single-herb herbal medicines wubeizi, *Lonicera japonica*, *Astragalus membranaceus*, *Rehmanniae Radix*, *Glycyrrhizae Radix* and *Panax schinseng* at a ratio of 1:1:1:1:1:1 by weight. The resulted mixture was the composition of the present invention.

Example 3

Anti-cancer Testing of the Herb Mixtures

Cell Lines

To examine the effects of the present composition SF-01 on inhibition of cancer/tumor cells, various human cell lines were used, including one normal cell line and eight cancer/tumor cell lines:
1. RPTEC (Cambrex): Normal renal proxima tubule epithelial cell, Human
2. A-498 (ATCC HTB-44): Kidney carcinoma, Human
3. HCT 116 (ATCC CCL-247): Colorectal carcinoma, Human
4. Hep 3B (ATCC HB-8064): Hepatocellular carcinoma, Human
5. LNCap clone FGC (ATCC CRL-1740): Prostate carcinoma, Human
6. MCF-7 (ATCC HTB-22): Mammary gland adenocarcinoma, Human
7. MKN45 (FDSC JCRB0245): Stomach carcinoma, Human
8. NCI-H226 (ATCC CRL-5826): Lung carcinoma, Human
9. NPC-TW01 (School of Medicine, NTU): Nasal-pharyngeal carcinoma, Human All of the cell lines used were negative for mycoplasma test. Among these cell lines, renal proximal tubule epithelial cell (RPTEC), the only normal cell line, were maintained in REGM™ BulletKit at 37° C. in a humidified atmosphere of 5% $CO_2$/95% air, in the absence of antibiotics according to the manufacture's recommendation. On the other hand, the eight tumor cell lines were maintained in DulBeccco's modified essential medium (DMEM) supplied with 10% fetal bovine serum at 37° C., in a humidified atmosphere of 5% $CO_2$/95% air in the absence of antibiotics.

Reagents

Fetal calf serum was purchased from BioWhittaker (Walkersville, Md.), MTS was obtained from Promega (Madison, Wis.). All of the other chemicals were from Sigma Chemical (St. Louis, Mo.) and were standard analytic grade or higher. SF-01 was dissolved in the complete culture medium at final concentration of 10mg/ml and was filter sterilized. Doxorubicin and Taxol were prepared in DMSO at concentration of 20 mM and were used as the positive controls.

To evaluate the antitumoral activity of SF-01 towards various human cancer cell lines and measure the potential cytotoxicity of SF-01 towards the primary human renal cell lines (RPTEC), an in vitro cytotoxicity assay was carried out. Tumor cells were seeded at a density of $2 \times 10^3$ to $8 \times 10^3$ cells/well in 96-well plate 16 hours prior to the chemicals treatment. After exposure to different concentrations of SF-01 (5.0 to 0.0016 mg/ml), Doxorubixin (10 μM to 3.2 nM) or Taxol (2 μM to 0.02 nM) for 72 hours, cells were washed, replaced with medium containing 0.4mg/MTS [3-(4,5-dimethylthiazol-2-yl)-5-(3-carboxymethosyphenyl)-2-(4-sulfophenyl)-2H-tetrazolium] and further incubated for 2 hours. To quantify the metabolically viable cells, the conversion of MTS to formazan was measured by absorbance at 490 nm in a 96-well microtiter plate reader. The mock-treated control was used to evaluate the effect of the chemical on cell growth and to determine the concentration of chemical that inhibited 50% of cell growth ($IC_{50}$). The percentage of cytostasis was calculated by the formula:

$$\text{Cytostasis } (\%) = [1 - (B/A)] \times 100,$$

where A is the absorbance of the untreated control and B is the absorbance of the treated cell.

Figure 2:
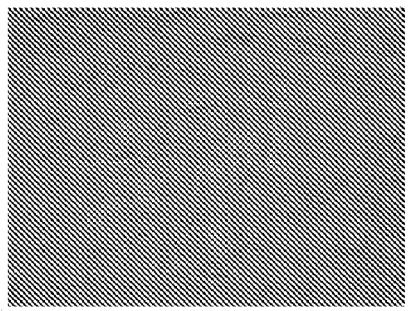
FIG. 2 shows the morphological effects of the composition of the present invention, Taxol and Doxorubicin on human cancer cell A498, HCT 116, Hep 3B, LNCaP clone FGC, MCF-7, MKN45, NCI-H226, NPC-TW01 and the human normal renal cell RPTEC.
Figure 2:
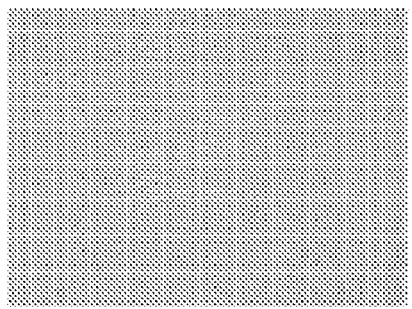
Figure 2:
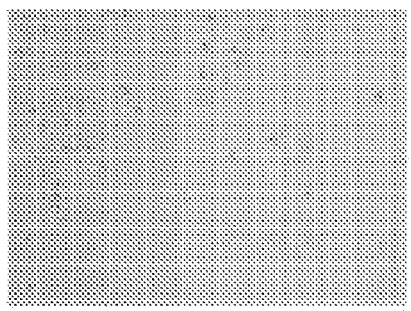
Figure 2:
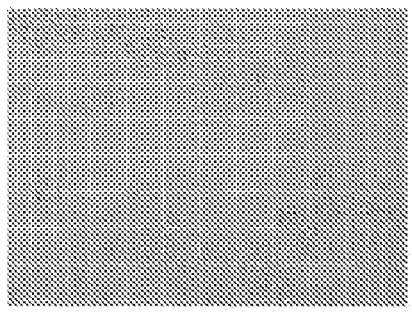
Figure 2:
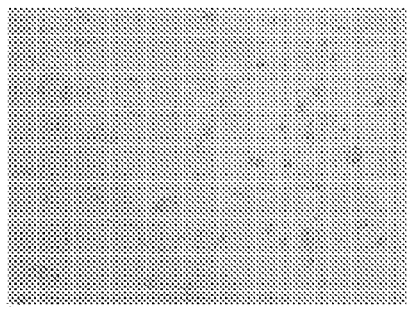
Figure 2:
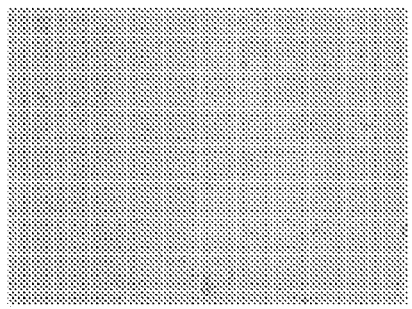
Figure 2:
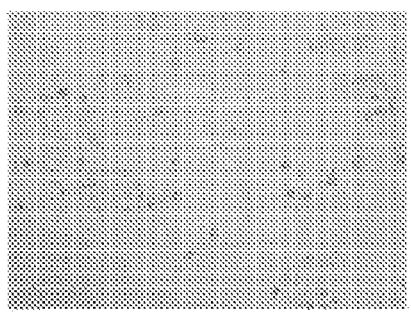
Figure 2:
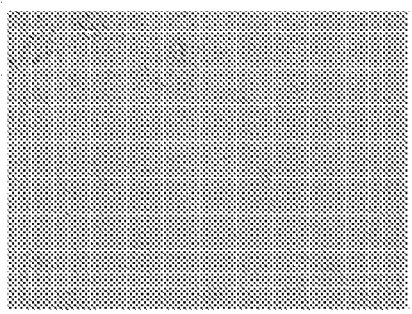
Figure 2:
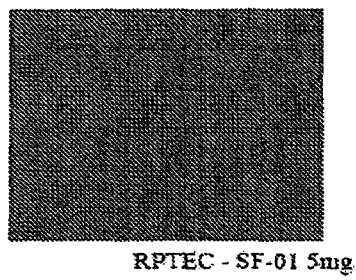
Figure 2:
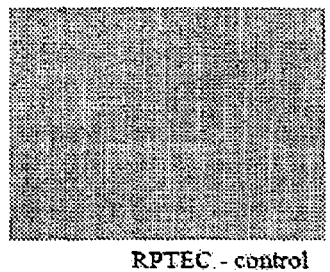
Figure 2:
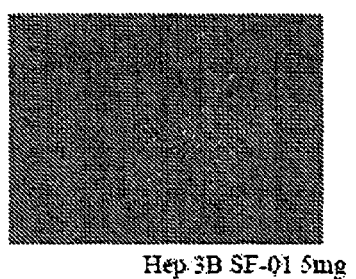
Figure 2:
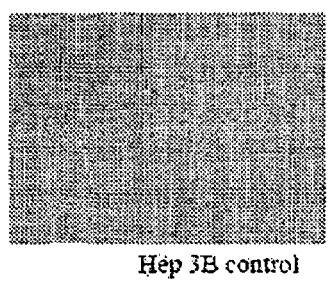
Figure 2:
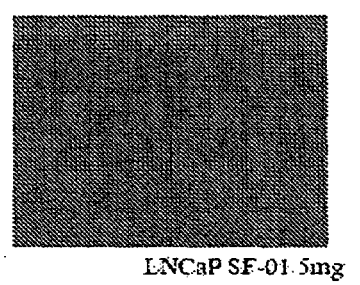
Figure 2:
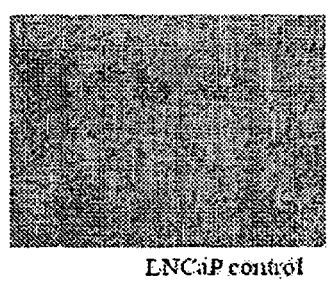
Figure 2:
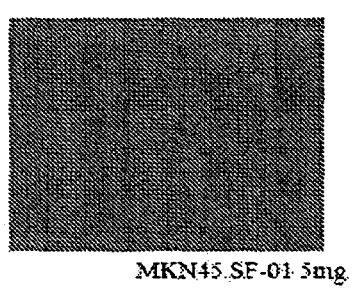
Figure 2:
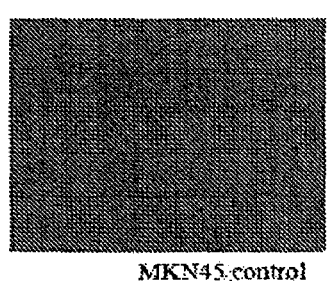
Figure 2:
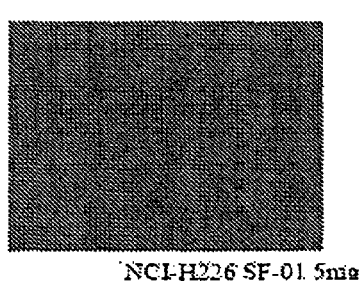
Figure 2:
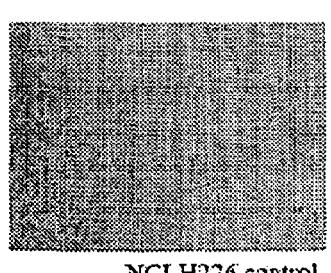

To evaluate the effects of the tested drugs on cell growth, the concentration of chemical that caused 50% reduction of the treated cells ($IC_{50}$) was calculated from the dose response curve (FIG. 1) for each cell line. The $IC_{50}$ for both Doxorubicin and Taxol to various human tumor cellines were found between 800 to 11 nM and 11 to 0.003 nM (Table 1) respectively, which was consistent with previously data. Our data showed that the cytotoxicity of SF-01 toward cancer cell line depends on the nature of the tumor cells, showing the selectivity of SF-01. Among all the tumor cell lines tested, MCF-7 was found to be most sensitive to SF-01, as the concentration of SF-01 as low as 0.59 mg/ml was able to cause 50% reduction of the treated cells, demonstrating the efficient antitumor activity of SF-01 on breast cancer cells. On the other hand, no noticeable morphological change or cytotoxicity was found when the normal cell line RPTEC was cultured with SF-01 for 72 hours compared to the untreated cells (FIG. 2). In addition, cell growth stimulation was found when RPTEC was cultured in higher concentration of SF-01. The results showed that SF-01 has little or no toxicity to the normal cells and also might promote its growth at higher concentration. This report was finished from Department of Toxicology and Preclinical Sciences, Pharmaceutical R&D Laboratories, Development Center for Biotechnology. No. 103, Lane 169, Kang Ning St. Hsichih city, Taipei county, Taiwan.

TABLE 1

The concentration of SF-01, Taxol and Doxorubicin that
inhibit 50% of cell growth ($IC_{50}$) of human cancer cell
A498, HCT 116, Hep 3B, LNCaP clone FGC, MCF-7, MKN45,
NCI-H226, NPC-TW01 and the human normal renal cell RPTEC.

| Cell line | $IC_{50}$ | | |
|---|---|---|---|
| | SF-01 (mg/mL) | Taxol (uM) | Doxorubicin (uM) |
| A498 | 4.59 | 0.0111 | 0.782 |
| HCT 116 | 2.85 | <0.0000256 | 0.033 |
| Hep 3B | 1.97 | 0.0000256 | 0.116 |
| LNCaP clone FGC | >5 | <0.0000256 | 0.014 |
| MCF-7 | 0.59 | <0.0000256 | 0.070 |
| MKN45 | 1.75 | 0.0000256 | 0.058 |
| NCI-H226 | 3.12 | <0.00064 | 0.123 |
| NPC-TW01 | 1.89 | <0.0000256 | 0.011 |
| RPTEC | >5 | 0.4059 | 3.18 |

What is claimed is:

1. A composition consisting of Wubeizi, *Lonicera japonica*, *Astragalus membranaceus*, *Rehmanniae Radix*, *Glycyrrhizae Radix* and *Panax ginseng*,
    wherein weight ratios of any two components range from 1:10 to 10:1;
    wherein Wubeizi is a gall produced by parasitic aphids *Melaphis chinensis* (Bell) Baker on a leave or stem of a plant selected from the group consisting of *Rhus chinensis* Mill, *Rhus potaninii* Maxim and *Rhus punjabensis* Stew. var. sinica (Diels) Rehd. et Wils.;
    wherein *Lonicera japonica* is prepared from flower buds of a plant selected from the group consisting of *Lonicera japonica* and *Lonicera confuse*,
    wherein *Astragalus membranaceus* is prepared from a root of a plant selected from the group consisting of *Astragalus membranaceus* (Fisch.) Bge. and *Astragalus membranaceus* Bge. var. mongholicus (Bge.) Hsiao;
    wherein *Rehmanniae Radix* is prepared from a root of *Rehmannia glutinosa* Libosch;
    wherein *Glycyrrhizae Radix* is prepared from a whole plant of a plant selected from the group consisting of *Glycyrrhiza uralensis* Fisch., *Glycyrrhiza glabra* L., *Glycyrrhiza kansuensis* Chang et Peng and *Glycyrrhiza inflata* Batal; and
    wherein *Panax ginseng* is prepared from the root of a plant selected from a group consisting of *Panax ginseng* and *Panax pseudoginseng*.

2. The composition of claim 1, wherein weight ratios of any two components range from 1:5 to 5:1.

3. The composition of claim 2, wherein weight ratios of any two components range from 1:3 to 3:1.

4. The composition of claim 3, wherein weight ratios of any two components are 1:1.

* * * * *